United States Patent
Hirayama et al.

(10) Patent No.: US 9,162,225 B2
(45) Date of Patent: Oct. 20, 2015

(54) MICROCHIP

(75) Inventors: Hiroshi Hirayama, Musashino (JP);
Takashi Washizu, Hino (JP); Naoki Shimizu, Hachioji (JP); Toshinori Takimura, Duluth, GA (US); Takehiko Goshima, Kunitachi (JP); Yoshiyuki Masuda, Hino (JP)

(73) Assignees: KONICA MINOLTA, INC., Tokyo (JP); Wako Pure Chemical Industries, Ltd., Osaka (JP)

( * ) Notice: Subject to any disclaimer, the term of this patent is extended or adjusted under 35 U.S.C. 154(b) by 54 days.

(21) Appl. No.: 13/260,728

(22) PCT Filed: Mar. 15, 2010

(86) PCT No.: PCT/JP2010/054321
§ 371 (c)(1),
(2), (4) Date: Sep. 27, 2011

(87) PCT Pub. No.: WO2010/116856
PCT Pub. Date: Oct. 14, 2010

(65) Prior Publication Data
US 2012/0020835 A1     Jan. 26, 2012

(30) Foreign Application Priority Data
Mar. 30, 2009 (JP) .................................. 2009-081511

(51) Int. Cl.
*G01N 35/08* (2006.01)
*B81B 1/00* (2006.01)
(Continued)

(52) U.S. Cl.
CPC ..... *B01L 3/502715* (2013.01); *B01L 3/502792* (2013.01);
(Continued)

(58) Field of Classification Search
USPC ........................ 422/68.1, 502–537; 435/287.2
See application file for complete search history.

(56) References Cited

U.S. PATENT DOCUMENTS

| 6,273,478 B1 | 8/2001 | Benett et al. |
| 2004/0091398 A1* | 5/2004 | Gilbert et al. ................ 422/100 |

(Continued)

FOREIGN PATENT DOCUMENTS

| EP | 2312321 A1 * | 4/2011 |
| JP | 2003-185627 | 7/2003 |

(Continued)

OTHER PUBLICATIONS

T. Kitamori, "Micro-Kagaku-chip No Gijutsu-to-Ohyou (Technology and Application of Micro Chemical Chip)", Maruzen Co., Ltd., 2004 with partial English translation.

*Primary Examiner* — Jennifer Wecker
(74) *Attorney, Agent, or Firm* — Cozen O'Connor (57) ABSTRACT

A microchip having a substrate, a cover member joined to one surface of the substrate, and a flow path formed on at least one of joined surfaces of the substrate and the cover member, wherein the microchip includes: a well which is an first opening for communicating into the flow path with a surface opposite to the joined surface of the substrate and is arranged on the substrate; and a chimney which is a member arranged so as to project from the surface opposite to the joined surface of the substrate and has an second opening which communicating into the well, wherein a liquid rise prevention section is formed in the chimney to prevent the liquid from rising to a top portion of the chimney.

5 Claims, 7 Drawing Sheets (51) Int. Cl.
   *B32B 3/02*      (2006.01)
   *B32B 3/30*      (2006.01)
   *B01L 3/00*      (2006.01)
   *B01J 19/00*     (2006.01)
   *G01N 37/00*     (2006.01)
   *G01N 35/10*     (2006.01)

(52) U.S. Cl.
   CPC ... *B01L 2200/027* (2013.01); *B01L 2200/0684* (2013.01); *B01L 2200/0689* (2013.01); *B01L 2200/141* (2013.01); *B01L2200/142* (2013.01); *B01L 2300/087* (2013.01); *B01L 2300/089* (2013.01); *B01L 2400/0688* (2013.01); *G01N 2035/102* (2013.01); *G01N 2035/1034* (2013.01)

(56) References Cited

U.S. PATENT DOCUMENTS

| | | | |
|---|---|---|---|
| 2006/0246573 A1* | 11/2006 | Kurane et al. | 435/287.2 |
| 2008/0248962 A1* | 10/2008 | Kim et al. | 506/9 |
| 2009/0155840 A1* | 6/2009 | Beebe et al. | 435/39 |
| 2011/0135538 A1* | 6/2011 | Goshima et al. | 422/68.1 |
| 2011/0135539 A1* | 6/2011 | Sekihara et al. | 422/68.1 |
| 2012/0052240 A1* | 3/2012 | Washizu et al. | 428/133 |

FOREIGN PATENT DOCUMENTS

| | | |
|---|---|---|
| JP | 2005-514187 | 5/2005 |
| JP | 2005-214782 | 8/2005 |
| JP | 2005-257544 | 9/2005 |
| JP | 2006-349347 | 12/2006 |
| JP | 2006349347 A * | 12/2006 |

* cited by examiner

MICROCHIP

RELATED APPLICATIONS

This application is a U.S. National Phase Application under 35 USC 371 of International Application PCT/JP2010/054321 filed Mar. 15, 2010.

This application claims the priority of Japanese application No. 2009-081511 filed Mar. 30, 2009, the entire content of which is hereby incorporated by reference.

TECHNICAL FIELD

The present invention relates to a microchip used for a chemical analysis system, and particularly to a microchip which effectively prevents stains caused by chemical reagents at an inlet at a time when injecting chemical reagents and the accompanying stains on the cover of the microchip.

BACKGROUND ART

In recent years, in a field of medical treatment or environment measurement, attention has been focused on a small-sized chemical analysis system which is affectionately known by an abbreviation of μTAS (Micro Total Analysis System) (non-Patent Document 1, etc), and development of a resin microchip which can be manufactured by injection molding or imprint molding is desired due to the reason that a mass production and a significant cost reduction are especially possible.

In the microchip used for the μTAS, there are usually formed a minute flow path which functions as a flow path of liquid, and a well (an orifice communicating between the minute flow path and outside) used for injecting liquid into the minute flow path, or ejecting liquid from the minute flow path (refer to, for example, Patent Documents 1 and 2).

A mode of the microchip includes a type in which only an orifice which functions simply as a well was opened on a planar chip, or a type in which a cylinder called a chimney was joined with the well or the cylinder and the well were integrally molded. In particular, in the case of a microchip having a chimney, the amount of liquid to inject, such as gel, a sample reagent and a sample can be secured, and then, it becomes possible to make connectivity with an analysis apparatus reliable and convenient.

How to use (usage) of a microchip having a chimney is, for example, as follows:
Step 1. Place a chip with the opening of the chimney facing upward.
Step 2. Inject liquid such as gel, a sample reagent and a sample, which is necessary for an analysis, with a needle into each chimney (in this case, there may be some chimneys into which no liquid is injected).
Step 3. Put covers on a certain number of chimneys, and introduce liquid such as gel, a sample reagent and a sample into minute flow paths by putting pressure or absorbing from other chimney.
Step 4. Move liquid in the minute flow paths by applying pressure or a voltage to the chip, to allow a reaction (such as stirring, synthesis, and separation) between each of liquids to proceed.
Step 5. Remove the cover, and just throw out the chip.

The usage of a microchip (having no chimney), in which simply an orifice (a well) was opened on the chip, is the same as the above, even if the amount of liquid to inject becomes small.

In the conventional laboratory level, basically no problem is caused even if a microchip is operated and used according to the above Steps 1 to 5. While, in the practical level, if we try to gain maximum merits such that reactions and analyses can be performed in a short time, there may be a case that a need to shorten the time of the above actions is caused, and in particular, there has been necessary to finish insertion of a liquid injection needle, injection of liquid, or pulling out the needle in a short time.

PRIOR ART

Patent Documents

Patent Document 1: Japanese Patent Application Publication No. 2005-257544
Patent Document 2: Japanese Patent Application Publication No. 2003-185627

Non-Patent Document

Non-Patent Document 1: Takehiko Kitamori, "Micro-Kagaku-chip No Gijutsu-to-Ohyou (Technology and Application of Micro Chemical Chip)," Maruzen Co. Ltd., 2004

SUMMARY OF THE INVENTION

Problem to be Solved by the Invention

Figure 12:
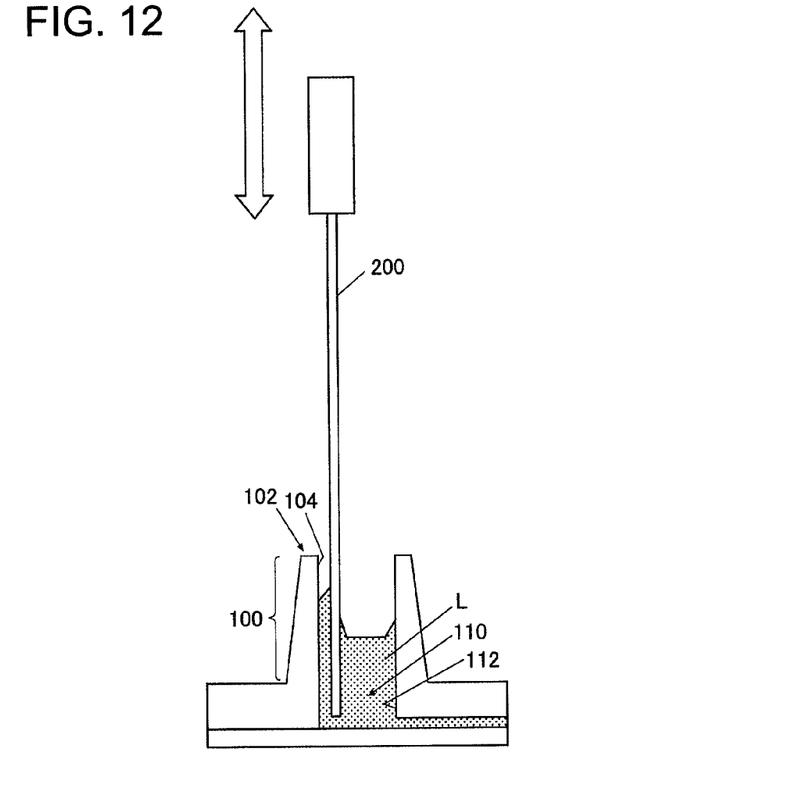
FIG. 12 is a figure to schematically describe the conventional problems.

In the case where a liquid injection needle was successfully inserted into the center portion of the chimney, no particular problem was caused. However, in the case where a positioning error of the microchip was caused, if needle 200 is inserted near inner wall 104 of chimney 100, as shown in FIG. 12, a phenomenon (so-called capillary action) that liquid L rises between inner wall 104 and needle 200 due to surface tension was shown. At that time, if needle 200 is quickly pulled out, liquid L is drawn by needle 200, which liquid then remains as liquid droplets by adhering to inner wall 104 near top portion 102 of chimney 100 or to top portion 102, and, when a cover is put on chimney 100, there was caused a phenomenon that the liquid droplets adhered to inner wall 104 or top portion 102 adhere to the cover (leak of liquid L, which volume was precisely measured, is caused).

In particular, in the microchip having no chimney, this phenomenon is prominent. Namely, in the case where a microchip has a chimney, even if a small amount of liquid L is drawn by the capillary action, it is somewhat possible to keep liquid L in the interior of chimney 100, since inner wall 104 of chimney 100 has a certain height. However, in the case where a microchip has no chimney, since the height of inner wall 112 of well 110 is short, liquid L easily springs out of well 110.

A cover to close the chimney or the well is basically equipped to the body of an analytical apparatus which is a different body from the microchip, and then, there are mainly two problems of adhering the liquid droplets to the aforesaid cover.

One of the two problems is that the quantitative performance of liquid such as gel, a sample reagent, and a sample is deteriorated, and another one is that the cover is stained by liquid such as gel, a sample reagent, and a sample, and thereby, when the microchip to be used next time is installed in the body of an analytical apparatus, the stain on the cover will cause a contamination.

To solve such problems, there may be a method to clean the cover every time a microchip is used (that is, an analysis is ended), but the method is not practical because the cleaning takes time and further it is difficult to achieve the perfect cleaning as well as increase in cost. In addition, a method may also be possible to heighten the positioning accuracy to insert or pull out a needle, but a future microchip is predicted that the integration degree of the well or the minute flow path will be increased and then the diameter of the chimney or the well will become smaller, and thereby, the above method should not be a fundamental solution.

Therefore, the main purpose of the present invention is to provide a microchip which has a chimney and can prevent or suppress adhesion of liquid to the top portion of the chimney associated with pulling out of a needle after injection of liquid.

Another purpose of the present invention is to provide a microchip having no chimney which can prevent or suppress adhesion of liquid to the upper surface near the opening at the exit side of the well associated with pulling out of a needle after injection of liquid.

Measures to Solve Problems

According to an embodiment of the present invention to solve the above problems, there is provided a microchip having a substrate, a cover member joined to one surface of the substrate, and a flow path formed on at least one of joined surfaces of the substrate and the cover member, wherein the microchip includes:

a well which is an opening for communicating into the flow path with a surface opposite to the joined surface of the substrate and is arranged on the substrate; and a chimney which is a member arranged so as to project from the surface opposite to the joined surface of the substrate and has an opening which communicating into the well, wherein a liquid rise prevention section is formed in the chimney to prevent the liquid from rising to a top portion of the chimney.

According to another embodiment of the present invention, there is provided a microchip having a substrate, a cover member joined to one surface of the substrate, and a flow path formed on at least one of joined surfaces of the substrate and the cover member, wherein the microchip includes:

a well which is an opening for communicating into the flow path with a surface opposite to the joined surface of the substrate and is arranged on the substrate; and a liquid rise prevention section to prevent the liquid from rising to an upper surface near the opening at an exit side of the well is formed on the substrate.

Effects of the Invention

According to one embodiment of the present invention, since a liquid rise prevention section is formed in the chimney, it is possible to prevent or suppress adhesion of liquid to the top portion of the chimney associated with pulling out of a needle after injection of liquid.

According to another embodiment of the present invention, since a liquid rise prevention section is formed on the well, it is possible to prevent or suppress adhesion of liquid to the upper surface near the opening at the exit side of the well associated with pulling out of a needle after injection of liquid.

BRIEF DESCRIPTION OF THE DRAWINGS

FIG. 6(*a*) is a sectional view along A-A line of FIG. 1, and a sectional view showing a schematic structure of the chimney used in the preferred embodiment of the present invention (the fifth embodiment) and its neighborhood.

FIG. 6(*b*) is an enlargement view of the part of the circle surrounded with the alternate long and short dash line shown in the FIG. 6(*a*).

MODE FOR CARRYING OUT THE INVENTION

First, terms used in the present invention will be described.

In the present invention, the term "well" indicates an opening which communicates between flow paths formed by being sandwiched between a substrate and a cover member and the outer surface of the substrate, that is, the surface opposite to the joined surface, and the shape of the well is not limited to a specific one. The phrase "the inner wall near the opening at the exit side of the well" indicates, among inner walls of the well, the side closer to the exit than the portion where liquid to be used as a sample reagent is filled, that is, an area near the opening at the opposite side of the joined surface.

In addition, in the present invention, the term "chimney" means a member which is arranged so as to project from the surface opposite to the joined surface of the substrate, and has an opening in communication with the above well, and the chimney generally has a tube shape. The shape of the chimney is not limited to a specific one, and includes a cylindrical shape if it is the tube type, or a square pillar shape in which an opening is arranged in the inner part, and the cylindrical shape is preferable from the viewpoint of formability or the like. Further, as the shape of the chimney, the so-called truncated cone or truncated pyramid in which the outer-diameter changes from the substrate side toward the top portion may be accepted.

The term "top portion of the chimney" indicates the upper surface portion around the opening at the exit side of the chimney, and the phrase "inner wall near the top portion of the chimney" shall indicates the inner wall portion of the side closer to the exit than the upper surface of filled liquid, when liquid to be used as a sample reagent is filled in the opening portion formed by the chimney and the well. Therefore, in the case where the upper surface of the filled liquid does not reach the inner wall of the chimney, that is, in the case where the height of the upper surface of the filled liquid is lower than the depth of the well, any portion of the inner surface of the chimney can be assumed to be an "inner wall near the top portion of the chimney," and the above liquid rise prevention section may be arranged at any place of the inner wall of the chimney.

Hereinafter, preferred embodiments of the present invention will be described with reference to figures.

Microchip (1) relating to the following embodiments is a microanalysis chip or an apparatus called a µTAS (Micro Total Analysis Systems), which forms minute flow paths or a circuit on one surface of a resin substrate utilizing a micromachining technology, and carries out, in a microspace, a chemical reaction, a separation or an analysis of a liquid sample such as nucleic acid, protein, or blood, and has been in progress for the practical application. In the embodiments, the microchip is described as being made of resin, but the material is not limited to a specific one, and a material such as glass can be used. However, the microchip is preferably made of resin from the viewpoint of formability.

The advantage of such a microchip may include realization of a portable and inexpensive system having a small-footprint, and in which the amount of use of a sample or a reagent or the amount of discharge of waste fluid can be reduced.

First Embodiment

Figure 1:
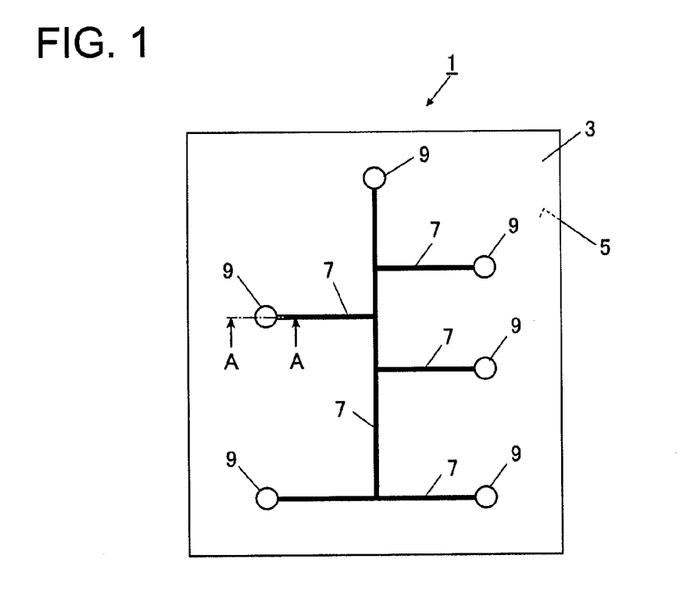
FIG. 1 is a plan showing a schematic structure of the microchip used in the preferred embodiment of the present invention.

As shown in FIG. 1, microchip 1 has a rectangular shape when viewed as a plane, and basically has a structure in which rectangular resin-made substrate 3 (the front side of the paper) and resin-made film 5, a cover member (the back side of the paper), are pasted to each other. In this structure, as the cover member, resin-made film 5 was pasted, but it is not limited to the film, and it is possible to seal the flow paths and wells by pasting a sheet-shape (a plate-like) member.

The outer shape of microchip 1 (resin-made substrate 3 and resin-made film 5) may be any one as long as it is easy to handle, or analyze, and a shape such as a square or a rectangular is preferable. As an example, the size may be 10 to 200 mm square. The size may also be 10 to 100 mm square.

Figure 2:
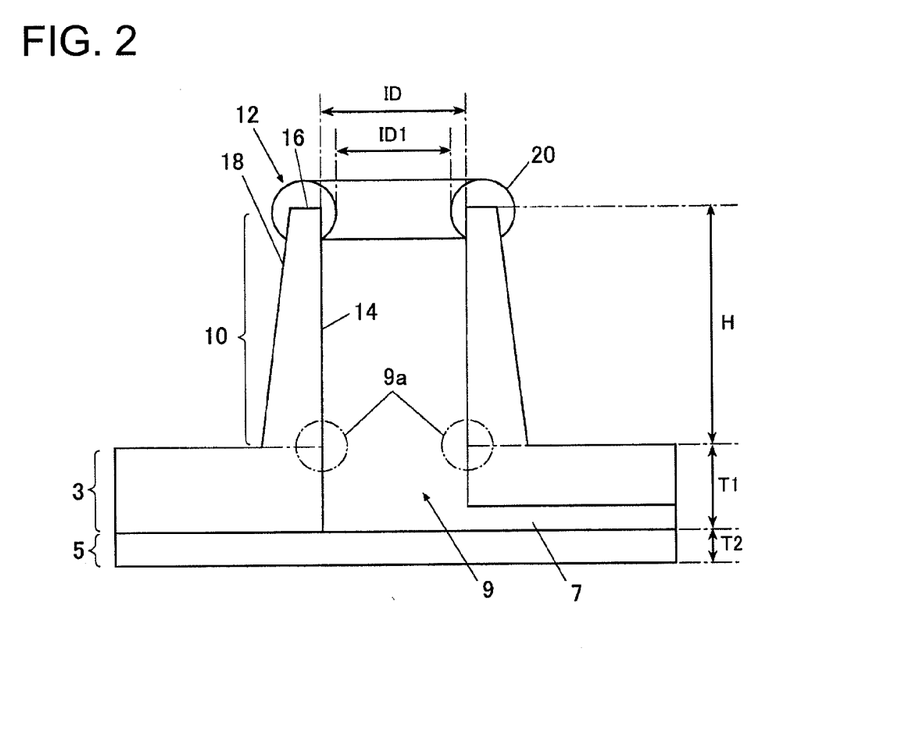
FIG. 2 is a sectional view along A-A line of FIG. 1, and a sectional view showing a schematic structure of the chimney used in the preferred embodiment of the present invention (the first embodiment) and its neighborhood.

In microchip 1, minute flow paths 7 and a plurality of wells 9 are formed. As shown in FIG. 2, minute flow path 7 is a flow path groove formed on resin-made substrate 3, and resin-made film 5 functions as a cover member (a cover) to form minute flow path 7. In the present embodiments, the flow path groove to form a flow path is arranged at the substrate (resin-made substrate 3) side, but it may be arranged at the cover member (resin-made film 5) side, or the grooves may be formed on the both substrate and the cover member.

Wells 9 are an orifice for liquid injection and discharge, which pass through resin-made substrate 3, and are in communication with minute flow paths 7.

The shape of minute flow path 7 preferably has both width and depth within a range of 10 to 200 µm, in consideration that the amount of use of an analytical sample or reagent can be reduced, and of manufacturing accuracy, transferability, releasability, or the like of a forming die, but is not limited to a specific one. The width and depth of minute flow path may be determined based on usage of microchip 1. The cross-sectional shape of minute flow path 7 may be a rectangular shape or a curved surface shape.

Board thickness T1 of resin-made substrate 3 is, in consideration of formability, preferably 0.2 to 5 mm, and more preferably 0.5 to 2 mm. Thickness T2 of resin-made film 5 (a sheet-like member) is preferably 30 µm to 300 µm, and more preferably 40 to 150 µm.

As shown in FIG. 2, on resin-made substrate 3, chimney 10 (a cylindrical body) having a prescribed height and exhibiting a cylindrical shape is arranged standing. Chimney 10 is integrally formed with resin-made substrate 3, and the internal space is in communication with well 9. As described above, in the embodiments, chimney 10 is described as a cylindrical body, but the shape is not limited.

Chimney 10 is structured separately from resin-made substrate 3, and may be united with resin-made substrate 3. To save the effort of glueing of chimney 10 to resin-made substrate 3, chimney 10 may be integrally formed with resin-made substrate 3.

Chimney 10 preferably has height H of about 1 to about 10 mm, and internal diameter ID (an opening size) of about 0.5 to about 5 mm. The "height H" of chimney 10 indicates a height from the surface (an upper surface) of resin-made substrate 3 to the top surface (an upper surface) of chimney 10, and the "internal diameter ID" indicates an internal diameter at the central part in the height direction of chimney 10.

Top portion 12 (a tip section) of chimney 10 exhibits a ring shape, and, at top portion 12, there is formed liquid rise prevention section 20 to prevent liquid from rising to the top portion of chimney 10.

Liquid rise prevention section 20 is constructed by UV curable resin (an adhesive), and is formed in a ring shape along top portion 12. Liquid rise prevention section 20, when viewed as a section, extends from inner wall surface 14 of chimney 10 through top surface 16 (an upper surface) to outer wall surface 18 to cover top portion 12. Therefore, internal diameter ID1 (an opening size) of top portion 12 of chimney 10 is configured to be smaller than internal diameter ID.

In this embodiment, the structure is made so as to cover top portion 12, but it may be made so as to project toward inner wall surface 14, and then, it may not be arranged at top surface 16 or outer wall surface 18.

In resin-made substrate 3 and resin-made film 5, resin is preferably used. As the resin, preferable conditions include excellent formability (transferability or releasability), high transparency, and low self-fluorescence to ultra-violet light or visible light. For example, thermoplastic resin is used for resin-made substrate 3 and resin-made film 5.

The thermoplastic resin preferably used includes, for example, polycarbonate, methyl polymethacrylate, polystyrene, polyacrylonitrile, polyvinylchloride, polyethylene-telephthalate, Nylon 6, Nylon 66, polyvinyl acetate, polyvinylidene chloride, polypropylene, polyisoprene, polyethylene, polydimethyl siloxane, or cyclic polyolefin. Particularly preferably used includes methyl polymethacrylate, or cyclic polyolefin. For both resin-made substrate 3 and resin-made film 5, the same material may be used, or different material may be used.

Subsequently, a method for manufacturing microchip 1 will be described.

As resin-made substrate 3, above certain resin is molded by injection molding using a certain die, and a plate-shaped resin molding having minute flow path 7, well 9, and chimney 10 is formed. In this case, to form chimney 10, a core pin having a certain tip diameter is erected on the movable core side.

On the other hand, as resin-made film 5, a film in which the above certain resin is cut to a prescribed size is prepared.

In the production (an injection molding) of resin-made substrate 3, an extraction taper of 2 to 5 degrees may be formed on flow path 7, well 9, and chimney 10 to enhance transferability.

After that, resin-made substrate 3 and resin-made film 5 are joined by thermal fusion bonding.

For example, using a heat plate, a hot air, a heat roll, an ultrasonic wave, a laser, or the like as the thermal fusion bonding, resin-made substrate 3 and resin-made film 5 are heated. An example of the joining is that resin-made substrate 3 and resin-made film 5 can be joined by sandwiching resin-made substrate 3 and resin-made film 5 with a heated heat plate using a heat pressing machine, which are then hold for a prescribed time with applying a pressure by the heat plate.

Due to such joining, resin-made film 5 functions as a cover for the flow path grooves, and then, minute flow paths are completely occluded. As a result, through the through-hole (well 9) and chimney 10, both of which were formed on resin-made substrate 3, minute flow path 7 is connected with the outside of the joined body composed of resin-made substrate 3 and resin-made film 5, and thereby it becomes possible to inject or discharge liquid sample.

After that, liquid rise prevention section 20 is formed near top portion 12 of chimney 10 of resin-made substrate 3. In details, the UV curable adhesive is applied in a ring shape along top portion 12 of chimney 10, and then, the aforesaid adhesive is cured by irradiating ultraviolet rays to the aforesaid adhesive. As a result, microchip 1 can be manufactured.

In the manufacturing liquid rise prevention section 20, since it is possible to manufacture it by applying and curing the adhesive, flexibility can be allowed in a change of the shape (such as internal diameter ID1).

According to the foregoing present embodiment, since liquid rise prevention section 20 is formed on inner wall surface 14 of (near) top portion 12 of chimney 10 and the opening diameter of chimney 10 is narrowed, liquid is brought back to the inside of chimney 10 by liquid rise prevention section 20 when a needle after injection of liquid is pulled out, and thereby, adhesion of liquid to (top portion 12 of) chimney 10 can be prevented or suppressed.

Second Embodiment

Figure 3:
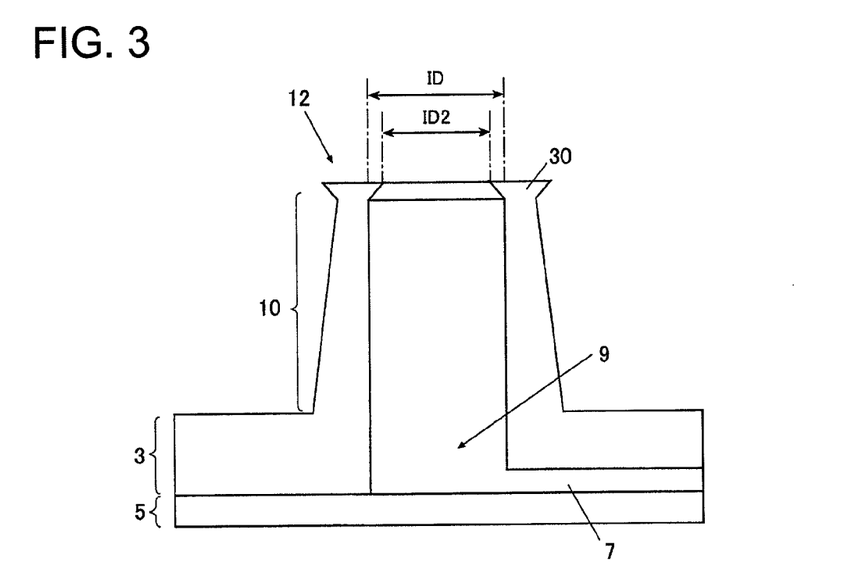
FIG. 3 is a sectional view along A-A line of FIG. 1, and a sectional view showing a schematic structure of the chimney used in the preferred embodiment of the present invention (the second embodiment) and its neighborhood.

The second embodiment differs from the first embodiment mainly in the following points, and the other parts are the same as those of the first embodiment. As shown in FIG. 3, in microchip 1 relating to the present embodiment, the structure of top portion 12 of chimney 10 differs from that of the first embodiment, and liquid rise prevention section 30 is arranged in place of liquid rise prevention section 20 of FIG. 2.

Liquid rise prevention section 30 is a portion in which top portion 12 of chimney 10 is transformed, and is formed integrally with chimney 10. Liquid rise prevention section 30 is a portion which is projected to both the inside and the outside of top portion 12 of chimney 10, and is formed in a ring shape along top portion 12 of chimney 10. Since liquid rise prevention section 30 is projected from the inner wall of chimney 10 to the inside, internal diameter ID2 (an opening diameter) of (near) top portion 12 of chimney 10 is made smaller than that of internal diameter ID.

When liquid rise prevention section 30 is manufactured, with keeping the side (the side of resin-made film 5), in which minute flow path 7 of resin-made substrate 3 was formed, at the normal temperature, a heat pressing machine (a heat plate) which is heated to a constant temperature is pushed against top portion 12 of chimney 10, and this state is kept for a certain time while applying a certain load, to heat transform top portion 12 of chimney 10.

In manufacturing liquid rise prevention section 30, since it is sufficient only to press a heat plate on top portion 12 of chimney 10, it can be relatively simply manufactured, and since the aforesaid heat plate and minute flow path 7 are separated by chimney 10, transformation of minute flow path 7 also can be prevented.

According to the present embodiment, similarly to the first embodiment, since liquid rise prevention section 30 is formed at top portion 12 of chimney 10 and the opening diameter of chimney 10 is narrowed, liquid is brought back to the inside of chimney 10 by liquid rise prevention section 30 when a needle after injection of liquid is pulled out, and thereby, adhesion of liquid to (top portion 12 of) chimney 10 can be prevented or suppressed.

Liquid rise prevention section 30 may be structured separately from chimney 10 and bonded to inner wall surface 14 of top portion 12 of chimney 10 as a projected part.

Third Embodiment

Figure 4:
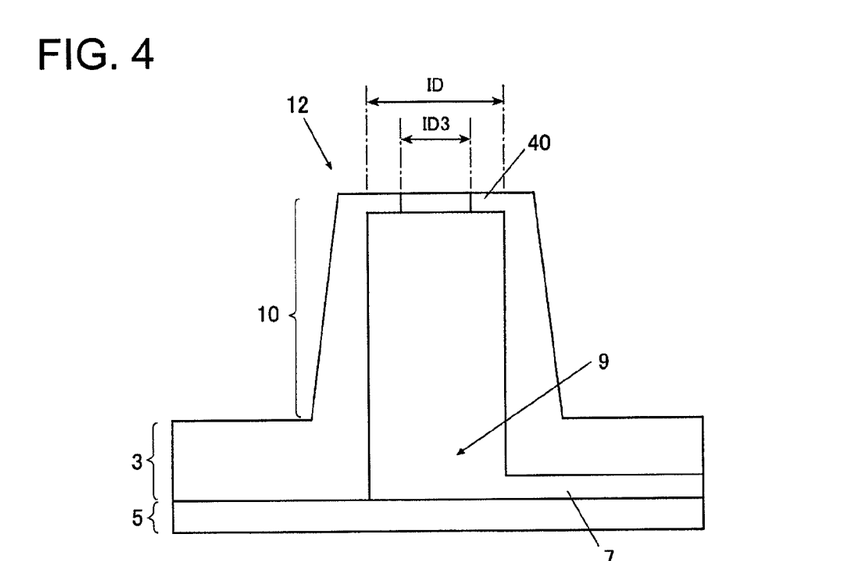
FIG. 4 is a sectional view along A-A line of FIG. 1, and a sectional view showing a schematic structure of the chimney used in the preferred embodiment of the present invention (the third embodiment) and its neighborhood.

The third embodiment differs from the first embodiment mainly in the following points, and the other parts are the same as those of the first embodiment. As shown in FIG. 4, in microchip 1 relating to the present embodiment, the structure of top portion 12 of chimney 10 differs from that of the first embodiment, and liquid rise prevention section 40 is arranged in place of liquid rise prevention section 20 of FIG. 2.

Liquid rise prevention section 40 is a portion in which top portion 12 of chimney 10 is transformed, and is formed integrally with chimney 10. Liquid rise prevention section 40 is a portion which is projected from the inner wall of top portion 12 of chimney 10 to the inside and is formed in a ring shape along top portion 12 of chimney 10.

Since liquid rise prevention section 40 is projected from the inner wall of chimney 10 to the inside, internal diameter ID3 (an opening diameter) of (near) top portion 12 of chimney 10 is made smaller than that of internal diameter ID.

When liquid rise prevention section 40 is manufactured, in a step of injection molding of resin (resin-made substrate 3), a core pin having a certain tip diameter is erected on the fixed core side, and a core pin having a tip diameter smaller than that of the core pin at the fixed core side is erected on the movable core side, and thereby the resin is molded by injection molding.

When liquid rise prevention section 40 is manufactured, since the formation is possible by selection and arrangement of a core pin in a step of injection molding of resin, accurate pattern transfer and stable quality can be secured compared to liquid rise prevention sections 20 and 30.

According to the foregoing present embodiment, since liquid rise prevention section 40 is formed at (near) top portion 12 of chimney 10 and the opening diameter of chimney 10 is narrowed, liquid is brought back to the inside of chimney 10 by liquid rise prevention section 40 when a needle after injection of liquid is pulled out, and thereby, adhesion of liquid to (top portion 12 of) chimney 10 can be prevented or suppressed.

Liquid rise prevention section 40 may be structured separately from chimney 10 and bonded to inner wall surface 14 of top portion 12 of chimney 10 as a projected part.

Fourth Embodiment

Figure 5:
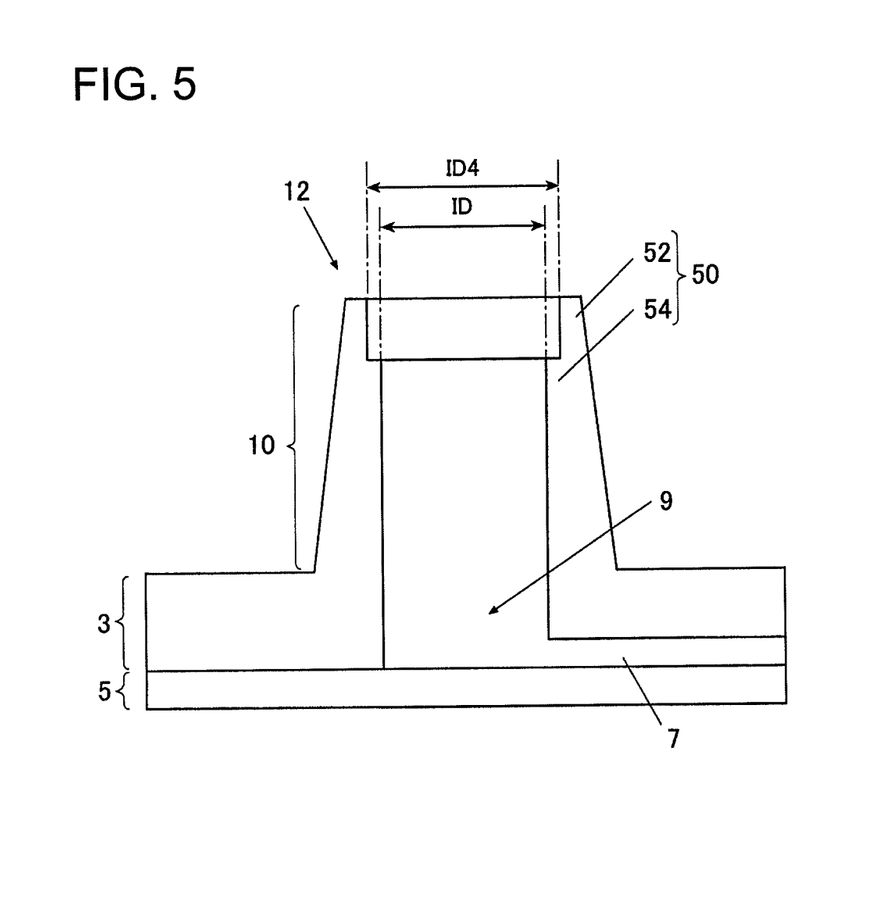
FIG. 5 is a sectional view along A-A line of FIG. 1, and a sectional view showing a schematic structure of the chimney used in the preferred embodiment of the present invention (the fourth embodiment) and its neighborhood.

The fourth embodiment differs from the first embodiment mainly in the following points, and the other parts are the same as those of the first embodiment. As shown in FIG. 5, in microchip 1 relating to the present embodiment, the structure of top portion 12 of chimney 10 differs from that of the first embodiment, and liquid rise prevention section 50 is arranged in place of liquid rise prevention section 20 of FIG. 2.

Liquid rise prevention section 50 is a portion in which top portion 12 of chimney 10 is transformed, and is formed integrally with chimney 10. Liquid rise prevention section 50 has a step structure along top portion 12 of chimney 10, and the internal diameter of (near) top portion 12 of chimney 10 is configured to be made larger. The step structure is composed of upper step portion 52 and lower step portion 54. The internal diameter (an opening diameter) of lower step portion 54 is equal to internal diameter ID of chimney 10, and internal diameter ID4 (an opening diameter) of upper step portion 52 is made to be larger than internal diameter ID of chimney 10.

When liquid rise prevention section 50 is manufactured, in a step of injection molding of resin (resin-made substrate 3), a core pin having a step is erected on the movable core side.

When liquid rise prevention section 50 is manufactured, since the formation is possible by selection and arrangement of a core pin in a step of injection molding of resin similarly to liquid rise prevention section 40, more accurate pattern transfer and more stable quality can be secured compared to liquid rise prevention sections 20 and 30.

According to the foregoing present embodiment, since liquid rise prevention section 50 is formed at top portion 12 of chimney 10, and thereby, the opening diameter of chimney 10 is expanded, a certain gap between the liquid injection needle and inner wall surface 14 of chimney 10 can be maintained. As a result, when a needle after injection of liquid is pulled out, the capillary effect between the needle and inner wall surface 14 can be suppressed, and thereby, adhesion of liquid to (top portion 12 of) chimney 10 can be prevented or suppressed.

In the present embodiment, liquid rise prevention section 50 was made into a step-like shape, but the shape is not limited to a specific one as long as the shape can restrain liquid rise by expanding the internal diameter of chimney 10. Also liquid rise prevention section 50 is not necessarily arranged at top portion 12, and may be arranged at a region closer to the exit side than a region where liquid is filled, that is, near top portion 12.

Fifth Embodiment

Figure 6A:
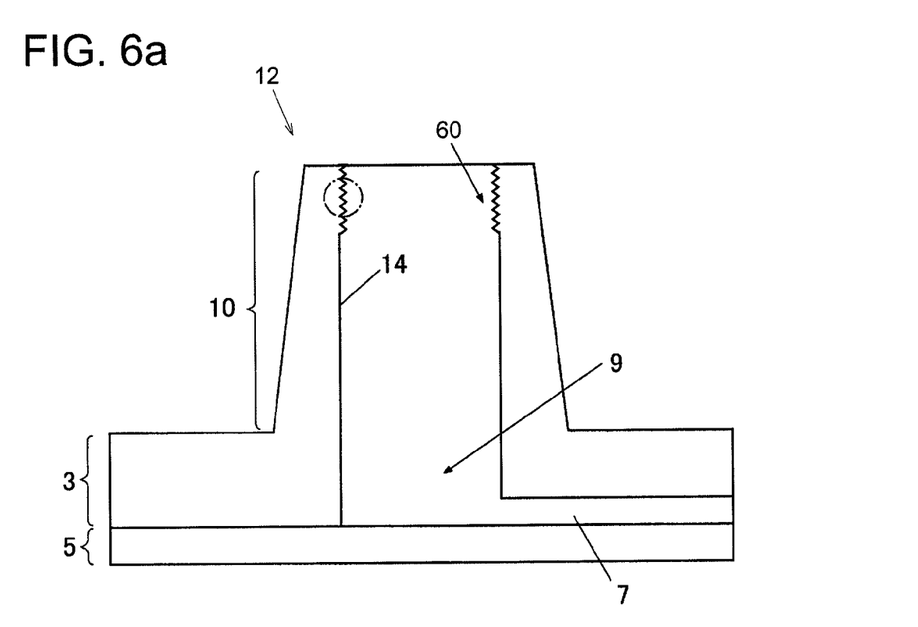

The fifth embodiment differs from the first embodiment mainly in the following points, and the other parts are the same as those of the first embodiment. As shown in FIG. 6*a*, in microchip 1 relating to the present embodiment, the structure of top portion 12 of chimney 10 differs from that of the first embodiment, and liquid rise prevention section 60 is arranged in place of liquid rise prevention section 20 of FIG. 2.

Liquid rise prevention section 60 is a portion in which inner wall surface 14 of (near) top portion 12 of chimney 10 is transformed, and is formed integrally with chimney 10. Liquid rise prevention section 60 is formed at inner wall surface 14 of top portion 12 of chimney 10 and in a ring shape along top portion 12. Liquid rise prevention section 60 is formed by surface texturing, and exhibits a concavo-convex shape. Namely, liquid rise prevention section 60 functions as a hydrophobic section by the concavo-convex structure.

When liquid rise prevention section 60 is manufactured, in a process of injection molding of resin (resin-made substrate 3), a core pin in which the tip was subjected to surface texturing is erected on the movable core side.

The arithmetic mean roughness of surface texturing of the core pin is preferably Ra=0.5 to 50 μm. The shape of the surface texturing of the core pin may be linear, curved, lattice-shaped, or an irregular intersection shape. In the case where the shape of surface texturing of the core pin is made into a lattice shape, the lattice spacing is preferably 10 to 200 μm.

In manufacturing liquid rise prevention section 60, since the formation is possible by selection of the core pin which was subjected to surface texturing, a uniform surface of surface texturing can be formed with excellent reproducibility, and, since control (optimization) can be made by physical properties of resin material, surface texturing patterns or roughness on the core pin, it is possible to control water repellency to top portion 12 of chimney 10 depending on liquid used.

According to the foregoing present embodiment, since liquid rise prevention section 60 is formed at top portion 12 of chimney 10, and top portion 12 exhibits a concavo-convex shape, water repellency is provided to inner wall surface 14 of (near) top portion 12 of chimney 10. As a result, when a needle after injection of liquid is pulled out, liquid rise between the needle and inner wall surface 14 can be suppressed, and thereby, adhesion of liquid to (top portion 12 of) chimney 10 can be prevented or suppressed.

Deformation Example

Figure 6B:
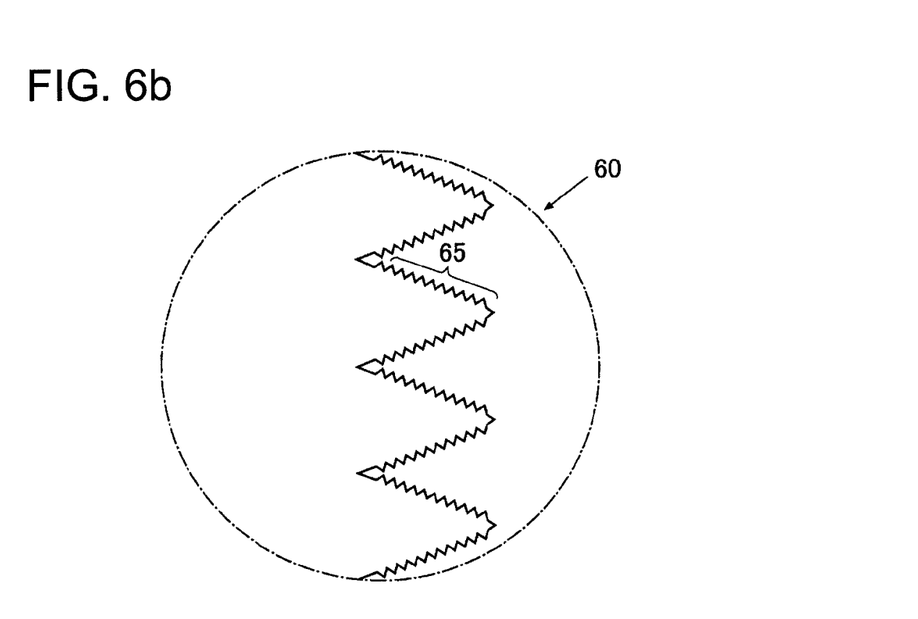

As shown in FIG. 6*b*, second concavo-convex structure 65 may further be formed on the surface of liquid rise prevention section 60, and thereby, the concavo-convex structure of liquid rise prevention section 60 may be made in two patterns. In this case, water repellency ability near top portion 12 of chimney 10 can be further improved.

Sixth Embodiment

Figure 7:
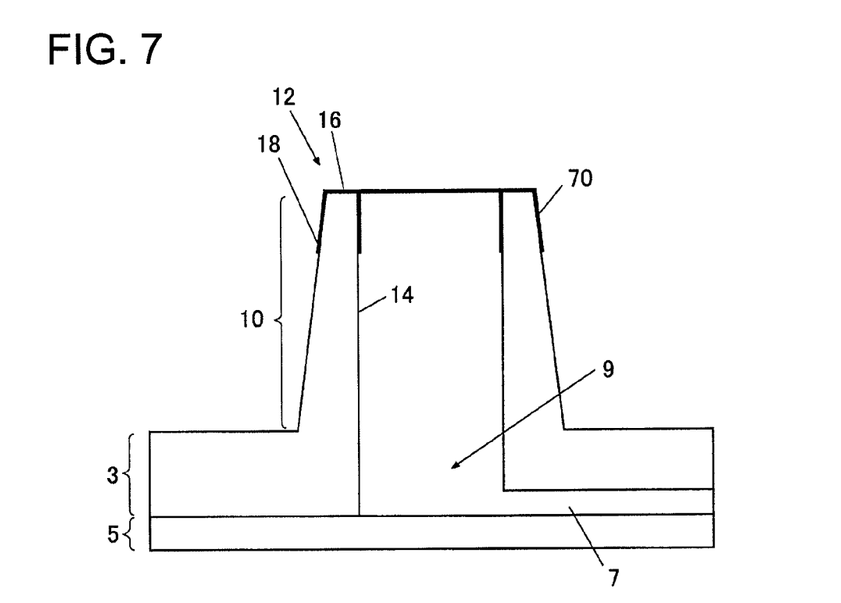
FIG. 7 is a sectional view along A-A line of FIG. 1, and a sectional view showing a schematic structure of the chimney used in the preferred embodiment of the present invention (the sixth embodiment) and its neighborhood.

The sixth embodiment differs from the first embodiment mainly in the following points, and the other parts are the same as those of the first embodiment. As shown in FIG. 7, in microchip 1 relating to the present embodiment, the structure near top portion 12 of chimney 10 differs from that of the first embodiment, and liquid rise prevention section 70 is arranged in place of liquid rise prevention section 20 of FIG. 2.

Liquid rise prevention section 70 is structured by a water repellent treatment film, and is functions as a hydrophobic section. Liquid rise prevention section 70 is formed in a ring shape along top portion 12. Liquid rise prevention section 70, when viewed as a section, extends from inner wall surface 14 of chimney 10 through top surface 16 (an upper surface) to outer wall surface 18 to cover top portion 12. The water repellence processing film, which composes liquid rise prevention section 70 is a film made of a fluorocarbon-based material.

In the present embodiment, the water repellence processing film is formed from inner wall surface 14 through top surface 16 to outer wall surface 18, but it may be arranged at least at inner wall surface 14.

When liquid rise prevention section 70 is manufactured, top portion 12 of chimney 10 is immersed in a certain fluoridation solution, followed by being dried. In manufacturing liquid rise prevention section 70, since liquid rise prevention section 70 can be formed by simply immersing top portion 12 of chimney 10 in the fluoridation solution, a uniform fluoridized surface can be formed at top portion 12 of chimney 10 with excellent reproducibility.

In order to enhance the adhesiveness between the water repellence processing film, which composes liquid rise prevention section 70, and the wall surface near top portion 12 of chimney 10, an $SiO_2$ film as an underlayer may be formed by a method such as vapor deposition and sputtering or a plasma processing may be performed on the wall surface of top portion 12.

The water repellence processing film, which composes liquid rise prevention section 70, is not limited to be made of a fluorocarbon-based material, and may be made of hydrocarbon-based material (for example, a DLC (diamond-like carbon) film), a Parylene coating (for example, Parylene coating manufactured by Japan Parylene Co.), or a triazine thiol film (for example, Triazinecoat, manufactured by Takeuchi Vacuum Deposition Co., Ltd.).

According to the foregoing present embodiment, since liquid rise prevention section 70 is formed near top portion 12 of chimney 10, and inner wall surface 14 near top portion 12 is covered by water repellence processing film, water repellency is provided to top portion 12 of chimney 10. As a result, when a needle after injection of liquid is pulled out, liquid rise between the needle and inner wall surface 14 can be suppressed, and thereby, adhesion of liquid to (top portion 12 of) chimney 10 can be prevented or suppressed.

Figure 8:
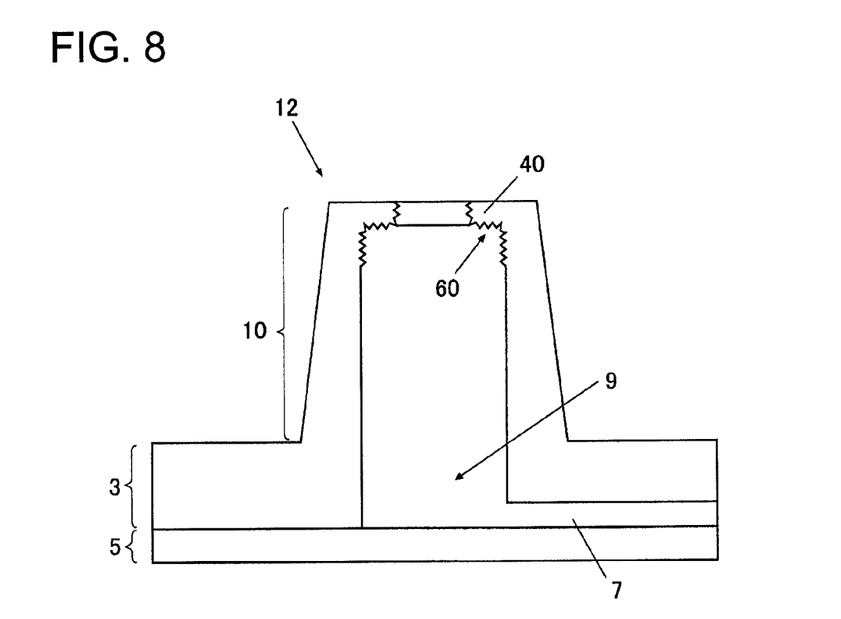
FIG. 8 is a sectional view showing a schematic structure relating to the combination between FIG. 4 and FIG. 6.
Figure 9:
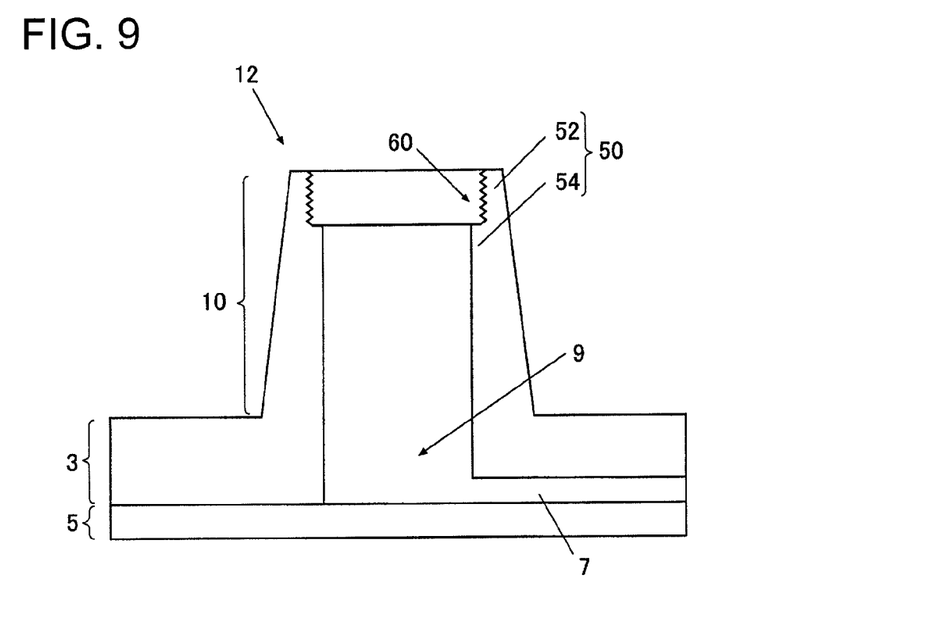
FIG. 9 is a sectional view showing a schematic structure relating to the combination between FIG. 5 and FIG. 6.
Figure 10:
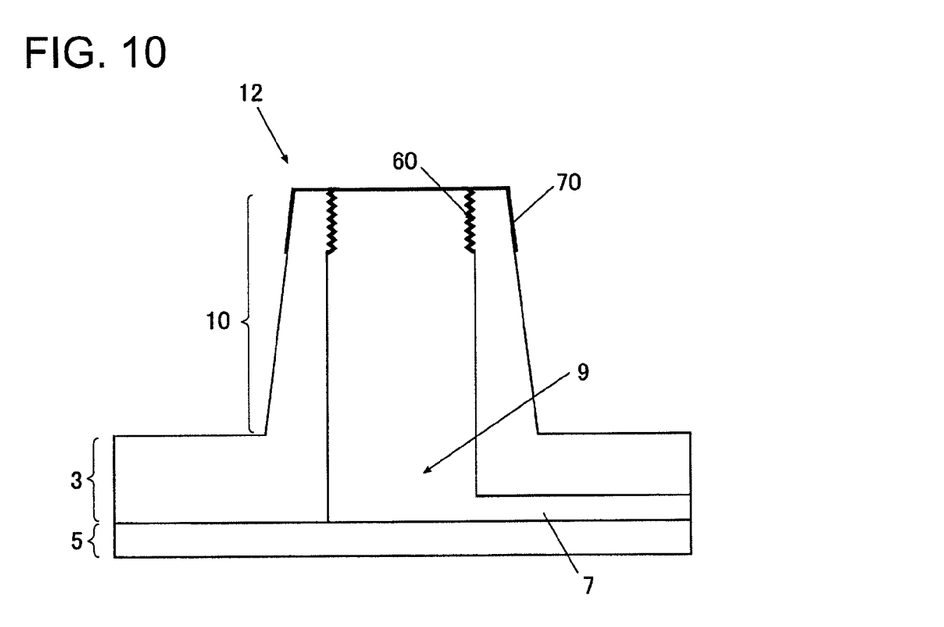
FIG. 10 is a sectional view showing a schematic structure relating to the combination between FIG. 6 and FIG. 7.

The structures relating to the first to sixth embodiments (liquid rise prevention sections 20, 30, 40, 50, 60, and 70) may be combined with each other. For example, at top portion 12 of chimney 10, there may be formed liquid rise prevention sections 40 and 60 at the same time as shown in FIG. 8, liquid rise prevention sections 50 and 60 at the same time as shown in FIG. 9, or liquid rise prevention sections 60 and 70 at the same time as shown in FIG. 10.

Further, the structures relating to the first to sixth embodiments (liquid rise prevention sections 20, 30, 40, 50, 60, and 70) are applicable to microchip 1 having no chimney 10, and near the opening at exit side of well 9, there may be formed liquid rise prevention sections 20, 30, 40, 50, 60, and 70 (including combinations thereof). As described above, the term "near the opening at exit side" of well 9 means the upper part than the liquid injection surface in well 9 and the part from the upper inner wall of well 9 to the upper surface of resin-made substrate 3 (refer to sign 9a in FIG. 2).

In this case, adhesion of liquid to (upper surface 9a near the opening of) well 9 associated with pulling out of a needle after injection of liquid can be prevented or suppressed.

EXAMPLES (1) Manufacturing of Samples (1.1) Sample 1

Figure 11:
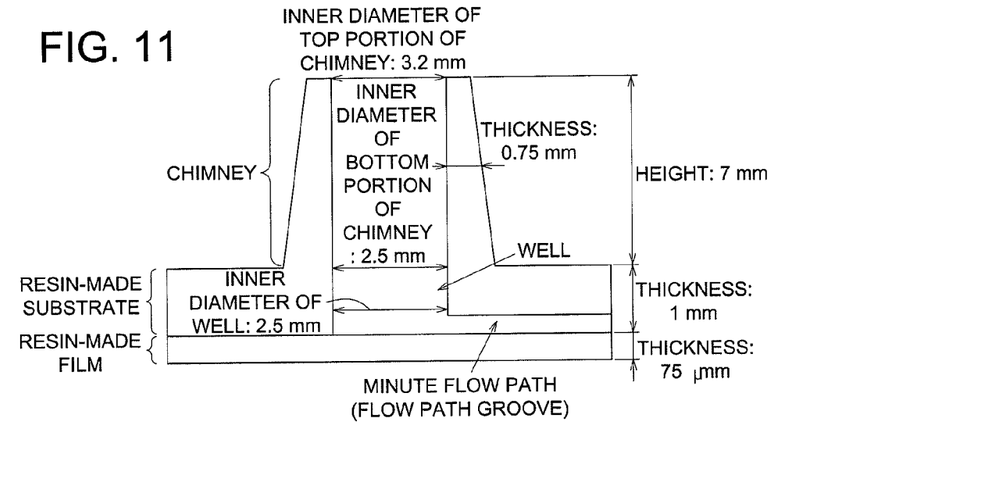
FIG. 11 is a sectional view showing a schematic structure relating to the basic structure (a comparative example) of the preferred example of the present invention.

As a resin-made substrate, polymethylmethacrylate (acryl-based resin, DELPET 70NH, manufactured by Asahi Kasei Corporation), a transparent resin material, was formed by injection molding, and a plate-like member having an external size of 50 mm in length×50 mm in width×1 mm in thickness was manufactured. On the plate-like member, the flow path grooves of 30 μm in width×30 μm in depth were formed, and further, a plurality of wells of 2.5 mm in inner diameter and a plurality of chimneys of 2.5 mm in inner diameter of bottom portion×7 mm in height×0.75 mm in (average) wall thickness were formed. On the flow path grooves and the chimney, an extraction taper of 2 to 5 degrees was formed to enhance transferability in the injection molding. As a result, whereas the inner diameter of bottom portion of the chimney is 2.5 mm, the inner diameter of top portion of the chimney became 3.2 mm (refer to FIG. 11).

On the other hand, as a resin-made film, a film of 50 mm in length×50 mm in width cut from polymethylmethacrylate (acryl-based resin, ACRYPLEN, manufactured by Mitsubishi Rayon Co., Ltd., with 75 μm in thickness), a transparent resin material, was prepared.

After that, the resin-made substrate and the resin-made film were put together. In details, the resin-made film was laid on the joining surface of the resin-made substrate on which the flow path grooves were formed, and then, the laminated resin-made substrate and resin-made film were sandwiched between heat plates which were heated to a pressing temperature of 82° C. using a heat press, on which a pressure of $3.72 \times 10^6$ Pa (38 $kgf/cm^2$) was applied and maintained for 30 seconds to put together the resin-made substrate and the resin-made film.

The microchip manufactured by the above processing was referred to as Sample 1.

(1.2) Sample 2

In Sample 1, a high viscosity UV adhesive was applied to the top portion of the chimney in a ring shape, which adhesive was then cured by irradiation of ultra-violet rays, to form a liquid rise prevention section having a ring shape (refer to FIG. 2). With this treatment, the inner diameter of top portion of the chimney was narrowed from 3.2 mm to 2.2 mm, which was referred to as Sample 2.

(1.3) Sample 3

In Sample 1, the shape of the top portion of the chimney was transformed to form the liquid rise prevention section (refer to FIG. 3). In Sample 1, with keeping the side where the flow path grooves of the resin-made substrate were formed at normal temperature, a heat press (a heated plate) which was heated to 150° C. was pushed against the top portion of the chimney and a load of 1 kg per well was added and maintained for 30 seconds.

With this treatment (by thermal deformation), the inner diameter of top portion of the chimney was narrowed from 3.2 mm to 2.4 mm, which was referred to as Sample 3.

(1.4) Sample 4

In Sample 1, the shape of the top portion of the chimney was transformed to form the liquid rise prevention section (refer to FIG. 4). In Sample 1, when the chimney was made, a core pin was erected on the movable core side, but, in this sample, a small diameter core pin of 2.2 mmϕ and a core pin having a tip diameter of 2.5 mm were erected on the movable core side and at the fixed core side respectively, to make the inner diameter of the top portion of the chimney 2.2 mm.

The microchip thus produced was referred to as Sample 4.

(1.5) Sample 5

In Sample 1, the shape of the top portion of the chimney was transformed to form the liquid rise prevention section (refer to FIG. 5). In Sample 1, when the chimney was made, a core pin was erected on the movable core side, but, in this sample, a core pin having steps was erected, and the size of the part having steps (the part having a larger inner diameter, an upper part) was made to be 3 mm in depth×4.2 mm in inner diameter×0.25 mm in wall thickness.

The microchip thus produced was referred to as Sample 5.

(1.6) Sample 6

In Sample 1, the shape of the top portion of the chimney was transformed to form the liquid rise prevention section (refer to FIG. 6a). In Sample 1, when the chimney was made, a mirrored core pin was erected on the movable core side, but, in this sample, a core pin which surface was subjected to surface texturing having arithmetic mean roughness of "Ra=10 µm" was erected. The core pin was subjected to surface texturing so that the surface texturing was made to the depth of 3 mm from the top portion (a top).

The microchip thus produced was referred to as Sample 6.

As a preliminary experiment, the water repellency of Sample 6 was determined as described below (a contact angle was measured).

A mirrored flat surface sample made of PMMA DELPET 70NH, the same material as the resin-made substrate of Sample 1, was prepared and a contact angle against pure water was determined to be 70°. After that, the flat surface sample was subjected to surface texturing having arithmetic mean roughness of Ra=10 µm, and then, a contact angle against pure water was determined to be 95°. It was confirmed that the contact angle increased from 70° to 95° before and after the surface texturing, indicating that the water repellency was provided.

(1.6.1) Regarding Sample 6-1

In Sample 6, a core pin which was subjected to surface texturing having arithmetic mean roughness of Ra=1 µm was used, and the microchip thus prepared was referred to as Sample 6-1.

As a preliminary experiment, the water repellency of Sample 6-1 was determined as described below. Each of a resin-made mirrored flat surface sample, a resin-made flat surface sample being subjected to surface texturing of Ra=1 µm, and a resin-made flat surface sample being subjected to surface texturing of Ra=0.3 µm was prepared.

After that, the above resin-made flat surface sample was arranged on one side, and a glass-made flat surface sample was arranged on the other side, and a gap of 0.1 mm was formed between each sample, in which sample, a liquid droplet (water) of 3 µl was introduced, and the penetration of the aforesaid liquid droplet into the gap was observed.

As a result of the observation, it was found that, whereas in the resin-made mirrored flat surface sample, the liquid droplet penetrated in less than one second, in a resin-made flat surface sample of Ra=1 µm, it took 2 seconds or more until the whole liquid droplet penetrated. In a resin-made flat surface sample of Ra=0.3 µm, the liquid droplet penetrated in less than one second.

As a result of the above observation, it was confirmed that, by performing the surface texturing of Ra=1 µm, an effect to suppress capillary action was provided.

(1.6.2) Regarding Sample 6-2

In Sample 6, a core pin which was subjected to surface texturing having a "lattice shape of 10 µm in height×150 µm in spacing" was used, and the microchip thus prepared was referred to as Sample 6-2.

As a preliminary experiment, the water repellency of Sample 6-2 was determined as described below. Each of a resin-made mirrored flat surface sample, a resin-made flat surface sample being subjected to surface texturing having a lattice shape (10 µm in height×150 µm in spacing), and a resin-made flat surface sample being subjected to surface texturing having a linear shape (10 µm in height×150 µm in spacing) was prepared.

The above resin-made flat surface sample was arranged on one side, and a glass-made flat surface sample was arranged on the other side, and a gap of 0.1 mm was formed between each sample, in which sample, a liquid droplet (water) of 3 µl was introduced, and the penetration of the aforesaid liquid droplet into the gap was observed.

As a result of the observation, it was found that, whereas in the resin-made mirrored flat surface sample, the liquid droplet penetrated in less than one second, in a resin-made flat surface sample having a lattice shape concavo-convex surface, the whole amount of liquid droplet never penetrated. In a resin-made flat surface sample having a linear shape concavo-convex surface, it took 5 seconds or more until the whole amount of liquid droplet penetrated (regarding a linear pattern, the whole amount never penetrated in the direction of crossing the line).

As a result of the above observation, it was confirmed that, by performing the surface texturing having a lattice shape (and a linear shape) on the surface, an effect to suppress capillary action was provided.

(1.7) Sample 7

In Sample 1, the top portion of the chimney was subjected to a fluorination treatment to form the liquid rise prevention section (refer to FIG. 7). Specifically, the top portion of the well was dipped for one minute at 3 mm in depth in a solution in which OPTOOL DX (manufactured by Daikin Industries, Ltd.) was diluted to 0.1% with DEMNUM solvent (manufactured by Daikin Industries, Ltd.), which was then dried for 24 hours, and further the resulting top portion was rinsed with DEMNUM solvent.

The microchip thus produced was referred to as Sample 7.

As a preliminary experiment, the water repellency of Sample 7 was determined as described below (a contact angle was measured). A mirrored flat surface sample was prepared with PMMA DELPET 70NH, the same material as the resin-made substrate of Sample 1, and a contact angle against pure water was determined to be 70°. After that, the flat surface sample was subjected to a fluorination treatment similarly to the above, and then, a contact angle against pure water was determined to be 108°. It was confirmed that the contact angle increased from 70° to 108° before and after the fluorination treatment, indicating that the water repellency was provided.

(1.8) Sample 8

In Sample 1, each of similar treatments to Sample 4 (reduction in the opening) and Sample 6 (surface texturing) was carried out to form the liquid rise prevention section (refer to FIG. 8).

In details, in the injection molding process of Sample 1, a core pin which was subjected to a surface texturing of Ra=10 µm with a diameter of 2.2 mmφ was erected on the movable core side, and a core pin which was subjected to a surface texturing of Ra=10 µm with a diameter of 2.5 mmφ was erected on the fixed core side, and the extent of surface texturing of a core pin was regulated so that the inner diameter of the top portion of the well was 22 mm and the surface texturing was performed on the portion of 3 mm in depth from the top portion of the well.

The microchip thus produced was referred to as Sample 8.

(1.9) Sample 9

In Sample 1, each of similar treatments to Sample 5 (formation of steps) and Sample 6 (surface texturing) was carried out to form the liquid rise prevention section (refer to FIG. 9). In details, in the injection molding process of Sample 1, a core pin which has steps and was subjected to a surface texturing of Ra=10 μm was erected on the movable core side so that the upper portion was made to be subjected to surface texturing with the dimension at the upper portion being 3 mm in depth× 4.2 mm in inner diameter×0.25 mm in thickness.

The microchip thus produced was referred to as Sample 9.

(1.10) Sample 10

In Sample 1, each of similar treatments to Sample 6 (surface texturing) and Sample 7 (fluorination treatment) was carried out to form the liquid rise prevention section (refer to FIG. 10). In details, in Sample 1, in the similar method to Sample 6, a surface texturing surface was formed in the inner wall of the top portion of the chimney, after which the inner wall of the top portion of the chimney was subjected to fluorination treatment by performing the similar treatment to Sample 7.

The microchip thus produced was referred to as Sample 10.

In Sample 10, when a similar preliminary experiment to that of Sample 6 was carried out, it was confirmed that the contact angle against pure water significantly increased from 70° to 135° before and after the surface texturing and fluorination treatment, indicating that the super water repellency was provided. The term "super water repellency" indicates a state such that when a drop of pure water is put on the surface, the droplet almost looks like a spherical shape, and when the flat surface sample is tilted, the droplet slides on the surface.

(2) Evaluation Methods and the Results

In each sample, examination was made on presence or absence of adherence of liquid to the chimney, where the liquid adhered to, the amount of the adhered liquid, or the like, and the quality of each sample was evaluated. In details, a syringe pump with a needle of 0.5 mmϕ in outer diameter× 0.25 mmϕ, in inner diameter×50 mm in length was first attached to the Z-axis stage. An aqueous solution, in which the viscosity was adjusted to 10 cP with a viscosity modifier, was put into the syringe. The needle was fixed to a position which was separated by 0.2 mm in the horizontal direction from the inner wall of the chimney and 50 mm in the vertical direction from the bottom portion of the well (the joint surface of the resin-made film with the resin-made substrate).

In this condition, actions were carried out in such a way that a needle was allowed to go down vertically at a rate of 300 mm/sec from the height of 50 mm from the bottom portion of the well to the height of 0.2 mm, and an aqueous solution of 15 μl was injected for 0.1 second, and after that, the needle was pulled out vertically to the outside of the well at a rate of 300 mm/sec, and thereby, presence or absence of adherence of liquid to the inner surface of the chimney, the top portion, or the like, where the liquid adhered to, the amount of the adhered liquid, or the like were confirmed (an adherence determination test).

The amount of the adhered liquid was calculated by weighing, using an accurate balance, a filter paper before and after absorption of the adhered liquid with the filter.

The outline (specifications) of the adherence determination test is as described below.

Needle: made of stainless steel, 0.5 mmϕ in outer diameter×0.25 mmϕ in inner diameter×50 mm in length Liquid: an aqueous solution with viscosity being adjusted to 10 cP using a viscosity modifier Rate of insertion and removal of needle: 300 mm/sec Injection amount of liquid: 15 μl Shape of well (Sample 1): 2.5 mm in inner diameter Shape of chimney (Sample 1): 2.5 mm in inner diameter of bottom portion×7 min in height×3.2 mm in inner diameter of top portion×0.75 mm in average thickness (1 mm in top portion thickness)

On each sample, the adherence determination test was repeated for 10 times, and the average (value) was determined. The results of the adherence determination test are described below for each sample, and, in addition, are simply shown in Table 1.

(2.1) Sample 1

As a result of the ten repetitions of the adherence determination test, the adherence of liquid droplet to the inner wall of the top portion of the chimney was observed. The average amount of adherence was 0.5 μl.

In particular, in two tests out of ten, the adherence to the top surface (the upper surface) was observed.

(2.2) Sample 2

As a result of the ten repetitions of the adherence determination test, adherence of liquid droplet to the lower portion of the liquid rise prevention section in the inner wall of the top portion of the chimney was slightly observed. The average amount of adherence was 0.2 μl.

In Sample 2, the reason for the above result can be assumed that, when pulling out of the liquid injection needle, the liquid drawn by the needle due to surface tension was returned to the inside of the chimney by the liquid rise prevention section in which the inner diameter was narrowed, and the part of it adhered to the lower portion of the liquid rise prevention section. Since no adhesion of liquid to the top surface (the upper surface) of the liquid rise prevention section was observed, it may be possible to prevent contamination.

(2.3) Sample 3

As a result of the ten repetitions of the adherence determination test, adherence of liquid droplet to the lower portion of the liquid rise prevention section in the inner wall of the top portion of the chimney was slightly observed. The average amount of adherence was 0.3 μl.

Also in Sample 3, similarly to Sample 2, the reason for the above result can be assumed that, when pulling out of the liquid injection needle, the liquid drawn by the needle due to surface tension was returned to the inside of the chimney by the liquid rise prevention section in which the inner diameter was narrowed, and the part of it adhered to the liquid rise prevention section. Since no adhesion of liquid to the top surface (the upper surface) of the liquid rise prevention section was observed, it may be possible to prevent contamination.

(2.4) Sample 4

As a result of the ten repetitions of the adherence determination test, adherence of liquid droplet to the lower portion of the liquid rise prevention section in the inner wall of the top portion of the chimney was slightly observed. The average amount of adherence was 0.2 μl.

Also in Sample 4, similarly to Sample 2, the reason for the above result can be assumed that, when pulling out of the liquid injection needle, the liquid drawn by the needle due to surface tension was returned to the inside of the chimney by the liquid rise prevention section in which the inner diameter was narrowed, and the part of it adhered to the lower portion of the liquid rise prevention section. Since no adhesion of liquid to the top surface (the upper surface) of the liquid rise prevention section was observed, it may be possible to prevent contamination.

(2.5) Sample 5

As a result of the ten repetitions of the adherence determination test, no adhesion to the top portion of the chimney (the inner wall of the liquid rise prevention section (the step structure section)) was observed.

It can be assumed that, since the needle could be separated from the inner wall of the chimney by a half of the expansion of the inner diameter of the upper part from 3.2 mmϕ to 4.2 mmϕ (by 0.5 mm), no adhesion phenomenon occurred.

(2.6) Sample 6

As a result of the ten repetitions of the adherence determination test, no adhesion to the top portion of the chimney was observed.

In Sample 6, the reason for the above result can be assumed that, by performing the surface texturing (Ra=10 μm), the contact angle against pure water of the inner wall of the top portion of the chimney increased from 70° to 95°, and thereby the water repellency against liquid was exhibited.

(2.6.1) Regarding Sample 6-1

As a result of the ten repetitions of the adherence determination test, no adhesion to the top portion of the chimney was observed.

In Sample 6-1, the reason for the above result can be assumed that, by performing the fine surface texturing (Ra=1 μm), the effect to suppress capillary action against liquid was exhibited.

(2.6.2) Regarding Sample 6-2

As a result of the ten repetitions of the adherence determination test, no adhesion to the top portion of the chimney was observed.

In Sample 6-2, the reason for the above result can be assumed that, by performing the surface texturing (a lattice-shape), the effect to suppress capillary action against liquid was exhibited.

(2.7) Sample 7

As a result of the ten repetitions of the adherence determination test, no adhesion to the top portion of the chimney was observed.

In Sample 7, the reason for the above result can be assumed that, by performing the fluorination treatment, the contact angle against pure water of the top portion of the chimney increased from 70° to 108°, and thereby the water repellency against liquid was exhibited.

(2.8) Sample 8

As a result of the ten repetitions of the adherence determination test, no adhesion to the top portion of the chimney was observed.

In Sample 8, the reason for the above result can be assumed that, when pulling out of the liquid injection needle, the liquid drawn by the needle due to surface tension was returned to the inside of the chimney by the liquid rise prevention section in which the inner diameter was narrowed, and at the same time, the top portion itself of the chimney was subjected to water repellency treatment by surface texturing.

(2.9) Sample 9

As a result of the ten repetitions of the adherence determination test, no adhesion to the top portion of the chimney was observed.

In Sample 8, the reason for the above result can be assumed that the needle could be separated from the inner wall of the chimney by a half of the expansion of the inner diameter of the upper part from 3.2 mmϕ to 4.2 mmϕ (by 0.5 mm), and further, the top portion of the chimney in which the inner diameter increased was in a state that liquid droplet was difficult to adhere since the top portion of the chimney was subjected to surface texturing.

(2.10) Sample 10

As a result of the ten repetitions of the adherence determination test, no adhesion to the top portion of the chimney was observed.

In Sample 10, the reason for the above result can be assumed that, by performing the surface texturing and fluorination treatment, the contact angle against pure water of the top portion of the chimney increased from 70° to 135°, and thereby the super water repellency against liquid was exhibited.

TABLE 1

| Sample | Mode of Liquid rise prevention section | Result of Evaluation State of Adherence to Chimney | Amount of Adhesion (μl) |
|---|---|---|---|
| 1 (Comparative Example) | — | Adhesion at Inner Wall of Top Portion and Top Surface was observed. | 0.5 |
| 2 (Example) | Contraction of Opening Size | Slight Adhesion at Inner Wall of Top Portion was observed. | 0.2 |
| 3 (Example) | | | 0.3 |
| 4 (Example) | | | 0.2 |
| 5 (Example) | Step Structure | No Adhesion was observed | — |
| 6 (Example) | Surface Texturing (Ra = 10 μm) | No Adhesion was observed | — |
| 6-1 (Example) | Surface Texturing (Ra = 1 μm) | No Adhesion was observed | — |

TABLE 1-continued

| Sample | Mode of Liquid rise prevention section | Result of Evaluation | |
|---|---|---|---|
| | | State of Adherence to Chimney | Amount of Adhesion (μl) |
| 6-2 (Example) | Surface Texturing (Lattice Shape) | No Adhesion was observed | — |
| 7 (Example) | Water-repellent Treatment Film | No Adhesion was observed | — |
| 8 (Example) | Contraction of Opening Size + Surface Texturing | No Adhesion was observed | — |
| 9 (Example) | Step Structure + Surface Texturing | No Adhesion was observed | — |
| 10 (Example) | Surface Texturing + Water-repellent Treatment Film | No Adhesion was observed | — |

(3) Summary

When Sample 1 is compared with Samples 2 to 10, Samples 2 to 10 showed excellent results.

From the above results, it was found that contraction of the opening diameter of the chimney, formation of a concavo-convex structure on the chimney, or formation of water-repellent treatment film on the chimney was useful in preventing or suppressing adhesion of liquid to the chimney.

In Samples 1 to 10, without forming the chimney, the similar treatment to Samples 2 to 9 was performed near the opening at exit side of the well, and then, the adherence determination test was carried out to each sample. As a result, the similar results to Samples 1 to 10 were obtained.

From the above results, it was found that contraction of the opening diameter of the well, formation of a concavo-convex structure on the well, or formation of water-repellent treatment film on the well was useful in preventing or suppressing adhesion of liquid to the well.

DESCRIPTION OF ALPHANUMERIC DESIGNATIONS

1. Microchip
3. Resin-made substrate
T1. Board thickness
5. Resin-made film
T2. Thickness
7. Minute flow path
9. Well
10. Chimney
12. Top portion
14. Inner wall surface
16. Top surface
18. Outer wall surface
H. Height
ID, ID1, ID2, and ID3. Inner diameter
20, 30, 40, 50, 60, and 70. Liquid rise prevention section
52. Upper step portion
54. Lower step portion
65. Second concavo-convex structure
100. Chimney
102. Top portion
104. Inner wall
110. Well
112. Inner wall
200. Needle
L. Liquid

What is claimed is:

1. A microchip having a substrate, a cover member joined to one surface of the substrate, and a flow path formed on at least one of joined surfaces of the substrate and the cover member, wherein the microchip comprises:
    a well which is a first opening for communicating into the flow path and which is arranged on the substrate; and
    a member which is arranged so as to project from the surface opposite to the joined surface of the substrate and has a second opening which communicates into the well,
    wherein a liquid rise prevention section comprising a step structure along a top portion of an inner wall of the member is formed in the member, said liquid rise prevention section configured to prevent a liquid from rising and adhering to the top portion of the member,
    wherein the step structure is provided with a lower step portion and with an upper step portion,
    wherein an opening diameter of the upper step portion is larger than an opening diameter of the lower step portion, and
    wherein the lower and upper step portions are discrete and form the second opening.

2. The microchip of claim 1, wherein the step structure is provided with a hydrophobic section along the top portion of the member.

3. The microchip of claim 2, wherein the hydrophobic section is constructed of a concavo-convex structure.

4. The microchip of claim 2, wherein the hydrophobic section is constructed of water repellent film.

5. The microchip of claim 1, wherein the member which is arranged so as to project from the surface opposite to the joined surface of the substrate is one of a cylindrical body, a tube shaped body, a square pillar shaped body, a truncated pyramid body, and a truncated cone body.

* * * * *